United States Patent [19]

Smith

[11] 4,063,558
[45] Dec. 20, 1977

[54] ARTICLE AND METHOD FOR MAKING HIGH FLUID-HOLDING FIBER MASS

[75] Inventor: Frederick R. Smith, Wilmington, Del.

[73] Assignee: Avtex Fibers Inc., Valley Forge, Pa.

[21] Appl. No.: 741,173

[22] Filed: Nov. 12, 1976

Related U.S. Application Data

[63] Continuation-in-part of Ser. No. 629,952, Nov. 7, 1975, and Ser. No. 696,451, June 15, 1976.

[51] Int. Cl.² ........................................... A61F 13/20
[52] U.S. Cl. .................................. 128/284; 106/194; 128/290 R; 264/188; 264/191; 428/288; 428/375; 428/378; 428/393; 428/913

[58] Field of Search .......................... 106/193 M, 194; 264/188, 191; 428/913, 288, 375, 364, 536, 378, 393; 128/284, 285, 270, 290 R

[56] References Cited

U.S. PATENT DOCUMENTS

| 3,187,747 | 6/1965 | Burgeni | 128/285- |
| 3,844,287 | 10/1974 | Smith | 264/188 |
| 3,951,889 | 4/1976 | Smith | 128/285 |

Primary Examiner—James J. Bell
Attorney, Agent, or Firm—Arthur R. Eglington

[57] ABSTRACT

Method for making alloy fibers having high fluid-holding capacity, the alloy fibers being comprised of a matrix of regenerated cellulose having alkali metal salts of alginic acid uniformly dispersed therein.

12 Claims, No Drawings

ARTICLE AND METHOD FOR MAKING HIGH FLUID-HOLDING FIBER MASS

CROSS REFERENCE

This application is a continuation-in-part of my applications Ser. No. 629,952, filed Nov. 7, 1975 and Ser. No. 696,451 filed June 15, 1976.

The present invention is directed to a method for making alloy fibers having high fluid-holding capacity.

Known in the art are alloy fibers, consisting of sodium polyacrylate and regenerated cellulose, which can be employed in various articles which are intended to absorb body liquids. While the fluid-holding capacity of these alloy fibers is greater than that of conventional regenerated cellulose fibers, this advantage is at least partially offset by their higher manufacturing costs.

Accordingly, a primary object is to provide a new or generally improved and more satisfactory method for making absorbent alloy fibers.

Another object is to provide a method for making absorbent alloy fibers of regenerated cellulose containing a uniform dispersion of alkali metal salts of alginic acid.

Still another object of this invention is the provision of a method for making absorbent alloy fibers from a mixture of viscose and alginate salts in which no special finishes and/or drying procedures are required.

As employed throughout the description and claims, the terminology "alloy fibers" refers to cellulose fibers having alkali metal salt alginates contained therein. Similarly, "fluid-holding capacity" is a measure of liquid absorbed into the fibers of a mass of alloy fibers, together with the liquid retained within the interstices of such fiber mass.

In accordance with the present invention, high fluid-holding alloy fibers are prepared by mixing an alkaline aqueous solution of an alkali metal alginate with a filament-forming viscose, shaping the mixture into fibers, coagulating and regenerating the shaped fibers and thereafter drying the same. Viscose constitutes the major portion of the mixture and the shaped alloy fibers are coagulated and regenerated by known means, and preferably in an acid bath containing sulfuric acid and sodium sulfate. Zinc sulfate is often incorporated in the bath as well as other coagulation modifiers, as desired. No special finishes and/or drying procedures are required to render the alloy fibers in a form which can be carded without difficulty.

The viscose which is employed in making the alloy fibers is, desirably, of a composition as is used in making conventional regenerated cellulose fibers. The composition of such viscose is well documented in the prior art and, in general, is produced by reacting alkali cellulose with carbon disulfide, with the resulting sodium cellulose xanthate being diluted with aqueous caustic to provide the resulting viscose with a desired cellulose and alkali content. Additives or modifiers may be mixed in the viscose, if desired.

Alkali-metal salts of alginic acid, which are suitable for use in the present invention, give in dilute NaOH solution or in aqueous solution, viscosities in the range of 20 to 150 seconds and preferably in the range of 40 to 80 seconds (Measurement of viscosity by time for a ⅛ inch diameter steel ball to fall 20 cm through the solution) with concentration of sodium alginate from 2 to 15% and preferably between 8 and 10%. The pH of an aqueous solution is preferably about or above seven.

In accordance with the present invention, the alginate as the solution is incorporated directly into a viscose and is employed in relatively large quantities, ranging from about 5 to about 30%, and is more desirable from above 10%, based upon the weight of the cellulose in the viscose. Fibers formed from a viscose containing less than about 5% of a useful alginate do not differ appreciably from conventional regenerated cellulose fibers in their fluid-holding capacity.

In accordance with the method of the present invention, aqueous solutions of alkali metal salts of alginic acid are injected into the viscose as it is pumped to spinnerets for extrusion.

Alternately, aqueous solutions of such alginates and viscose may be passed through a blender or homoginizer if it is necessary to secure a more uniform dispersion. After the spinning, coagulation, and regeneration stages, the shaped continuous tow of filaments undergoes the usual processing, which may include stretching if desired, and is then dried by conventional means. Generally, gefore drying, the continuous tow of filaments is cut into staple of a desired length.

In general, the resulting alloy fibers experience no bonding during drying, and can be subsequently carded with no difficulty by the manufacturer of absorbent articles incorporating such fibers. Alternatively, after coagulation, and at least partial regeneration, the fibers are stretched, if desired, conventionally wet processed and treated with an aqueous lubricating finish composition. The fibers are then dried to an alkaline, cardable product. In the preferred method of this invention, the sodium alginate dispersed in viscose, during processing into fibers, is alternately in the alkaline state, the acid state and again the alkaline state. During passage of the modified viscose through the acidic coagulating and regenerating bath, the sodium alginate is acidified. In order to obtain alkaline fibers containing sodium alginate, as required by the invention, the wet gel fibers are made alkaline preferably in a bath preceding the finish bath, or, if desired, in the finish bath.

Sodium salts of alginic acid, suitable for use in this invention, are commercially available from the Kelco Division of Merck & Co., under the designation Keltex alginates, sold in various grades as determined by viscosity and concentration in aqueous dispersions.

EXAMPLE I

Using conventional rayon spinning equipment, an alkaline aqueous solution of sodium alginate was separately injected by a metering pump into a viscose stream during its passage through the blender, the blend was thereafter extruded into a spinning bath.

Preparation of a 10% concentration of sodium alginate solution was as follows: 300 g. of sodium alginate (KELTEX) high viscosity technical grade Kelco Alginate were added to 300 ml of 18% concentration of aqueous sodium hydroxide plus 90 ml of 30% concentration hydrogen peroxide. The peroxide serves to reduce molecular weight and viscosity. This system, after mixing with a spatula, was added to 2250 ml of water, while stirring, and mixed for 2 hours.

After overnight standing at room temperature, it was mixed again for 2 more hours. The ball-fall viscosity after 48 hours was 24 seconds. The polymer was added to the viscose and spun by injection as described above. During this stage, the blend was subjected to high mechanical shearing. The viscose composition was 9.0% cellulose, 6.0% sodium hydroxide and 32% carbon disulfide (based upon weight of cellulose). The viscose ball-fall was 61 and its common salt test was 6.6.

The mixtures of viscose and sodium alginate were extruded through a 980 hole spinneret into an aqueous spinning bath consisting of 7.5% by weight of sulfuric acid, 20% by weight of sodium sulfate, and 1.5% by weight of zinc sulfate. After passage through the spinning bath, the resulting continuous tow was washed with water, desulfurized with an aqueous solution of sodium hydrosulfide, and again washed with water. The still wet multifilament tow was cut into staple fibers and finished with a solution comprising 1% $NaHCO_3$, 0.5% Span 20 and water. The fiber was then dried.

The fluid-holding capacity of sample fibers, made with various approximate proportions (tabulated below) of cellulose and sodium alginate in the spinning solution, was determined using the following test procedure.

Two and one-half grams of the different fibers prepared as described above were separately made into tampons by the following procedure: The fibers were carded into webs, each having a length of about 6 inches and being of variable thickness and width. Each of these webs was individually rolled in the direction of its width to provide a 6-inch roll and a string was looped about the center therof. Each such roll was then folded on itself at the string loop and drawn into a ½-inch tube within which it was compressed by a clamp and plunger. After compression, the resulting tampons were removed, allowed to stand for a period of about 30 minutes during which the tampons recovered to a bulk density of about 0.4 g/cc. and were then evaluated for their capacity to hold water by the Syngyna Method, as described by G. W. Rapp in a June 1958 publication of the Department of Research, Loyola University, Chicago, Illinois. The results of such test are set forth in Table I for fibers made with various approximate proportions (as tabulated in Table I) of cellulose and sodium alginate in the spinning solution.

EXAMPLE II

An aqueous solution of sodium alginate (prepared from a granular form supplied by the Keltex Co.) was made by dissolving Keltex in water to give 3% solution. The solution was injected into viscose, whereby the spinning solution contained 11.1% sodium alginate, based on cellulose. The fibers produced were subsequently processed in different ways and evaluated for fluid-holding capacity.

A portion of the resulting alloy rayon tow was treated with 1% aqueous $Na_2CO_3$ and 1% Span 20 (Sorbitan monolaurate) in one solution and dried. Sample staple fibers were carded, or otherwise well opened, and then conditioned at 75° F and 58% relative humidity. Two grams of such alloy fibers were placed in a one-inch diameter die, pressed to a thickness of 0.127 inch, and maintained in this condition for 1 minute. This compressed pellet of fibers was removed from the die and placed on a porous plate of a Buchner funnel. The upper surface of the pellet was then engaged with a plunger which was mounted for free verticle movement, the plunger having a diameter of 1 inch and a weight of 2.4 pounds.

The funnel stem was connected by a flexible hose to a dropping bottle from which water was introduced into the funnel to wet the pellet of fibers. Control over the water flow was exercised by the position of the dropping bottle. After an immersion period of 2 minutes, the water was permitted to drain from the fiber pellet for 3 minutes, after which the still wet pellet was removed from the funnel and weighed. One-half of the weight of water in the sample pellet is a measure of the fluid-holding capacity of the fibers, expressed in cc/g. This measurement is defined as the potential ratio.

A blend of equal parts of this sample fiber with a three denier crimped rayon (U.S. Pat. No. 3,046,983) had a potential ratio for 4.28 cc/g. The rayon control sample (no alginate loading) had a potential ratio of 2.7 cc/g.

The aqueous alkaline lubricating finish is often a bath containing an aqueous solution of sodium carbonate and sorbitan monolaurate; however, other alkaline agents and lubricating agents may be employed as taught in the art for ordinary rayon yarn. Alternatively, good control of product and process is maintained by separating the alkalizing and finishing treatment steps.

Some examples of finishes for cellulose fibers include partial higher fatty acid esters of sorbitan or mannitan and their polyoxyethylene derivatives, sodium oleate and oleic acid. Some examples of alkaline agents for alkalizing the fibers include dibasic ammonium phosphate, dibasic sodium phosphate, tribasic sodium phosphate, sodium tetraborate, and the like.

The alloy fibers made by the method of the present invention are adapted for use in a variety of articles, such as sanitary napkins and tampons, in which high fluid retention is an essential characteristic. In the manufacture of such articles, the alloy fibers necessitate no special techniques or equipment and they may be blended with other fibers which may or may not enhance the absorbent properties of the resulting articles. Fibers with which the alloy fibers may be blended include, for example, rayon, cotton, chemically modified rayon or cotton, cellulose acetate, nylon, polyester, acrylic, polyolefin, etc.

It is to be understood that changes and variations may be made without departing from the spirit and scope of the invention as defined in the appended claims. t,0090

What is claimed is:

1. An article of manufacture comprising a highly fluid absorbent mass of alkaline alloy fibers comprising a matrix of regenerated cellulose and an alginic acid salt of alkali-metals dispersed therein, said salt being present in an amount of at least about 5 weight percent based on the weight of the cellulose.

2. The article of claim 1 wherein the alginic acid salt of alkali-metals is present in the regenerated cellulose in an amount ranging from about 5 to about 30 weight percent, based on the weight of the cellulose.

3. The article of claim 1 wherein the fibers have a lubricating finish for cellulose thereon.

4. The article of claim 1 in the form of a pad.

5. The article of claim 1 in the form of a tampon.

6. An article as in claim 3 wherein said fibers are carded staple fibers, said article comprising a compressed mass of said staple fibers.

7. An alkaline alloy fiber comprising a matrix of regenerated cellulose and alginic acid salt of alkali-metals, said fiber having a lubricating finish for cellulose thereon said salt being such, and present in such proportion, within the range of about 5 to about 30 percent based on the weight of cellulose, that the "fluid-holding capacity" is at least 4.79 cc./g.

8. Fiber as in claim 7, said fiber being in staple form, said alkali-metal being in sodium form and said salt being present in amount of at least 10% based on weight of cellulose.

9. A method of preparing highly absorbent alloy fibers comprising mixing an alginic acid salt of alkali-metals with a filament-forming viscose whereby the viscose predominates in the mixture, forming the mixture into fibers, coagulating and regenerating the fibers, applying a lubricating finish for cellulose to said fibers, and drying the fibers in an alkaline state with said alginic acid salt in said fiber in the form of an alkali-metal salt, the proportion of said alginic acid salt added to said viscose being at least about 5% based on cellulose.

10. Method as in claim 9 wherein said alkali-metal salt in said dried alkaline fibers is such, and present in such proportion, that the "fluid-holding capacity" is at least 4.79 cc./g.

11. Method as in claim 10 wherein said salt in said alkaline fibers is a sodium salt.

12. Method as in claim 11 and including the step of cutting the fiber tow into staple form before drying.

* * * * *

UNITED STATES PATENT AND TRADEMARK OFFICE
CERTIFICATE OF CORRECTION

PATENT NO. : 4,063,558
DATED : December 20, 1977
INVENTOR(S) : Frederick R. Smith It is certified that error appears in the above-identified patent and that said Letters Patent are hereby corrected as shown below:

In column 4, after line 41, insert:

TABLE I

| SAMPLE | CELLULOSE | SODIUM ALGINATE | FLUID-HOLDING CAPACITY cc/g |
|--------|-----------|-----------------|------------------------------|
| A | 100 | 0 | 4.0 |
| B | 90 | 10 | 4.79 |
| C | 80 | 20 | 5.34 |
| D | 70 | 30 | 4.92 |
| E | 60 | 40 | 4.51 |

Signed and Sealed this

Twentieth Day of May 1980

[SEAL]

Attest:

Attesting Officer

SIDNEY A. DIAMOND

Commissioner of Patents and Trademarks